(12) United States Patent
Dourdeville et al.

(10) Patent No.: US 8,622,437 B2
(45) Date of Patent: Jan. 7, 2014

(54) FLUIDIC TERMINAL

(75) Inventors: Theodore Dourdeville, Marion, MA (US); Dennis DellaRovere, Mendon, MA (US)

(73) Assignee: Waters Technologies Corporation, Milford, MA (US)

( * ) Notice: Subject to any disclaimer, the term of this patent is extended or adjusted under 35 U.S.C. 154(b) by 883 days.

(21) Appl. No.: 11/348,857

(22) Filed: Feb. 6, 2006

(65) Prior Publication Data

US 2006/0151998 A1 Jul. 13, 2006

Related U.S. Application Data

(63) Continuation of application No. PCT/US2004/025659, filed on Aug. 6, 2004.

(60) Provisional application No. 60/492,952, filed on Aug. 6, 2003.

(51) Int. Cl.
*F16L 39/00* (2006.01)
*F16L 47/02* (2006.01)

(52) U.S. Cl.
USPC .............. 285/124.3; 285/124.1; 285/293.1

(58) Field of Classification Search
USPC .............. 210/198.2, 198.3; 285/293.1, 294.1, 285/124.1–124.5; 156/293
See application file for complete search history.

(56) References Cited

U.S. PATENT DOCUMENTS

| | | | | |
|---|---|---|---|---|
| 2,313,074 A * | 3/1943 | Jewell | ...................... | 285/294.3 |
| 4,090,899 A * | 5/1978 | Reich | .............................. | 156/79 |
| 4,268,041 A * | 5/1981 | Sovish et al. | .................. | 277/314 |
| 4,526,686 A * | 7/1985 | Sisti et al. | .................. | 210/198.2 |
| 4,690,437 A | 9/1987 | Anderson, Jr. | | |
| 5,194,225 A * | 3/1993 | Muller et al. | .................... | 422/70 |
| 5,237,735 A * | 8/1993 | Grossmann et al. | ......... | 29/522.1 |
| 5,288,113 A | 2/1994 | Silvis et al. | | |
| 5,482,628 A * | 1/1996 | Schick | ........................ | 210/198.2 |
| 5,568,949 A * | 10/1996 | Andre | ........................ | 285/285.1 |
| 5,578,157 A | 11/1996 | Higdon | | |
| 5,744,100 A * | 4/1998 | Krstanovic | .................... | 422/537 |
| 6,056,331 A * | 5/2000 | Benett et al. | .................. | 285/343 |
| 6,162,362 A * | 12/2000 | Ma et al. | ....................... | 210/656 |
| 6,290,791 B1 * | 9/2001 | Shaw et al. | ..................... | 156/64 |
| 6,367,847 B1 * | 4/2002 | Dourdeville et al. | ....... | 285/125.1 |
| 6,457,855 B1 | 10/2002 | Beirau et al. | | |
| 6,575,501 B1 * | 6/2003 | Loy, Jr. | ........................ | 285/342 |
| 6,585,296 B1 * | 7/2003 | Picha et al. | ................. | 285/124.1 |
| 6,926,313 B1 * | 8/2005 | Renzi | .............................. | 285/353 |
| 7,014,222 B1 * | 3/2006 | Poppe | ........................ | 285/332.1 |
| 7,125,461 B2 * | 10/2006 | Czaplicki et al. | ............... | 156/79 |

(Continued)

FOREIGN PATENT DOCUMENTS

WO    WO 96/12546    5/1996

*Primary Examiner* — James Hewitt
(74) *Attorney, Agent, or Firm* — Schmeiser, Olsen & Watts LLP (57) ABSTRACT

The invention comprises a terminal and a method for making such a terminal for placing one or more fluidic conduits in communication. The invention comprises a conduit for transporting fluid having a proximal and a distal end and a substantially cylindrical housing with an axial bore and a proximal face, the proximal end of the conduit being housed within the axial bore with their axes parallel, and the bore being back-filled with a thermoplastic polymer, most preferably PEEK, liquefied and cooled providing for the conduit to breach the sealing face and the thermoplastic to bond the conduit and housing.

18 Claims, 5 Drawing Sheets

(56) References Cited

U.S. PATENT DOCUMENTS

| | | | |
|---|---|---|---|
| 2002/0179513 A1* | 12/2002 | Willis et al. | 210/198.2 |
| 2004/0238447 A1* | 12/2004 | Cheong | 210/656 |
| 2007/0000828 A1* | 1/2007 | Norman et al. | 210/198.2 |
| 2007/0164562 A1* | 7/2007 | Valaskovic et al. | 285/245 |

* cited by examiner

FLUIDIC TERMINAL

CROSS REFERENCE TO RELATED APPLICATIONS

This application claims benefit of and is a continuation of International Application No. PCT/US2004/025659, filed Aug. 6, 2004 and designating the United States, which claims benefit of a priority to U.S. Provisional Application No. 60/492,952, filed Aug. 6, 2003. The contents of these applications are expressly incorporated herein by reference in its entirety.

FIELD OF THE INVENTION

The present invention relates generally to fluidic terminals, and more particularly to a method and apparatus for implementing junctions between fluid conduits, where the junctions are characterized by low dead volume, mechanical robustness, appropriate alignment, and ease of assembly, as is useful in the art of liquid chromatography, particularly at a capillary size scale.

BACKGROUND OF THE RELATED ART

In conventional-scale liquid chromatography, the mobile phase liquid is usually conveyed between components of the chromatography system in tubing constructed from stainless steel, polyether-ether-ketone (PEEK), or Teflon®. Conventional-scale chromatography is practiced with analytical columns having a typical internal diameter in the range of 3.9 to 4.6 millimeters. An industry-standard external diameter for interconnection tubing is nominal $1/16^{th}$ inch (approximately 0.062" or 1.59 mm)

The internal diameter of the interconnection tubing will generally vary with the type of application, but diameters ranging from 0.005" to 0.040" (0.127 to 1.02 mm) are common. Where liquid-tight connections need to be made between tubes, or between tubes and other structures such as flow cells, columns, or pumps, the sealing interface is often implemented with a compression-type fitting.

Typically, a conventional union is a junction effected between two stainless steel tubes. Stainless steel is a rugged tube material which can be fabricated with a burr-free, square polished end having a substantially right-circular cylindrical form. The union is also constructed from stainless steel and has a compression-type port detail machined into each end.

The cylindrical tube end is inserted into the union until it bottoms in a corresponding flat-bottomed counterbore feature within the port. The insertion depth of the tube is thereby controlled by the depth of the counterbore feature. A deformable ferrule, typically having a conical form, is slid over the tube to a point where it is interposed between the tube and a corresponding conical cavity within the compression port. A compression screw, which is free to rotate and translate over the tube outer diameter, engages a corresponding threaded region of the compression port.

Tightening of the compression screw deforms the ferrule in such a way as to effect a substantially liquid-tight seal between the outer diameter of the tube and at least a portion of the conical cavity of the compression port. The seal thus formed is therefore slightly removed from the actual tube end. The material chosen for the deformable ferrule will vary with the tubing material choice, and with the operating pressure specification, with stainless steel, PEEK, Teflon®, or Vespel® being typical candidate materials. Unions, tees, crosses, and other parts based on compression fitting interfaces are commercially available for industry-standard tube sizes. As is the case with tubing and ferrules, the unions, tees, and other components are manufactured from a variety of materials which address a range of working pressures and chemical compatibilities.

At a conventional liquid chromatography size scale, the tubing and associated parts, such as ferrules and compression screws, are of dimensions which can be readily manipulated by hand in the user's laboratory. Where interconnection tubing engages other tubes or fluid conduits, the alignment requirements are moderate. For example, the interface between two tubes of 0.010" internal diameter would tolerate misalignment of several thousandths of an inch without resulting in either blockage of the flow path, or serious degradation of the fidelity of chromatographic zones or bands, where the volume of the band is typically several hundred microliters.

Misalignment at the level of several thousandths of an inch can result from the diametral clearance which is required to facilitate assembly of a tube into a compression port, or from concentricity error introduced between the respective internal and external diameters of a tube during the tube manufacturing process. At conventional chromatography scale, maintaining the necessary fluid path alignment is possible with conventional design and machining practices, where attention is paid to the tolerance of the individual components and component clearances.

In recent years, interest has continued to grow in the practice of liquid chromatography at capillary size scales, where the internal diameter of the analytical column may range from 800 microns (micrometers) to 50 microns or less. For a column of 75 micron internal diameter, the volume of an eluting zone or band will typically be less than 100 nanoliters, or several thousand times less than in a conventional-scale chromatographic separation. In order to effect connections between components of a system incorporating a 75 micron diameter column, the connecting tubing will typically be chosen to have an internal diameter of 25 microns (approximately 0.001") or less.

The number of materials from which practical tubing of 15 to 25 micron internal diameter can be formed or drawn, while maintaining the necessary strength, smoothness, concentricity, solvent resistance, and cost, is relatively few. Fused silica is one such material, and fused silica tubing is commercially available in a variety of internal and external diameters suitable for use in liquid chromatography at the capillary size scale. Commercial fused silica tubing is typically provided with a polyimide buffer coating which provides a degree of mechanical protection to the external surface of the tubing.

While fused silica tubing has many desirable properties, its use in high-pressure liquid chromatography applications is hampered by several difficulties. When cut to length in the field, fused silica tubing is typically scored or nicked with a diamond tool, and then fractured. A poorly-cleaved end usually exhibits one or more projecting shards of fused silica, or projecting flaps of polyimide sheath. Deviation from a right-circular cylindrical form makes it difficult to achieve a joint between tubes, or between tubes and other structures, which does not suffer from poorly swept or "dead" volumes. Dead volumes degrade the fidelity of chromatographic zones which elute past the joint, resulting in broad peaks with correspondingly diminished chromatographic resolution. With time, poorly cleaved fused silica tubing ends may continue to fracture back, releasing fragments of fused silica and polyimide buffer coating, and further widening the gap between the tube end and the adjoining structure. Fused silica or polyimide fragments that become entrained in the liquid flow may cause blockages downstream which render the system inoperable.

Achieving adequate alignment of fluid paths at capillary scale junctions is also problematic. Within the liquid chromatography industry, adaptor sleeves and corresponding ferrules have been developed which are intended to provide a sealing interface between fused silica tubing and conventional compression-type ports. Such sleeves are typically constructed from PEEK, and most commonly are sized with the intent of adapting a fused silica tube of roughly 0.015" outer diameter to a compression port originally intended for nominal 0.062" outer diameter tubing.

In practice, the utility of these adaptor sleeves and ferrules is limited. The fused silica tubing itself will often demonstrate reasonably good concentricity between the internal and the external diameters. However, from spool to spool, the external diameter will typically vary over a range as defined by the product specification, but that may be of the order of tens of microns. This tolerance in outside diameter is accommodated by a corresponding clearance dimension designed into the internal diameter of the adaptor sleeve, so that the sleeve can be assembled onto the tube in the field. Correspondingly, there is typically a clearance introduced between the outside diameter of the adaptor sleeve and the internal diameter of the port detail where the sleeve engages it, so that the parts can be assembled in the field. As the adaptor sleeve is subjected to localized compression from the ferrule, the deformation may result in the fused silica tubing being biased toward one side.

Further reduction in the clearance dimensions is impractical, as the assembler is confronted with having to manage the insertion of a component of typically 0.015" diameter, and to accomplish that insertion without damaging the fragile end of the fused silica, or skiving PEEK or other material from the internal surface of the adaptor, thereby generating fragments which could obstruct the fluid path.

Even in the absence of alignment error resulting from the accumulation of component clearances, there is typically a concentricity error introduced between the inner and outer diameters of the adaptor sleeve itself. As a result, when a given fused silica tube is installed into a compression-type fitting using the adaptor sleeve and ferrule approach, the registration between the lumen or fluid path of the fused silica tubing and the fluid path of the mating part may be so poor as to effectively block the fluid path.

One industry-standard approach to circumventing fluid path blockage arising from errors in alignment of the respective fluid conduits meeting in a device such as a union, is to utilize a relatively larger diameter for the through-hole which penetrates the central web of the union. The diameter of this hole can be chosen to be large enough so that even in the presence of the largest expected accumulated positioning error, continuity of the fluid path can be guaranteed. This prior art approach may avoid obstruction of the fluid path, but tends to produce a junction with excessive band-broadening characteristics when employed at smaller volume scales. The discontinuity in flow path geometry encountered by the chromatographic band as it transits the enlarged central region of the union typically results in poor flushing characteristics with corresponding negative impact on band shape.

Another approach to circumventing fluid path blockage arising from errors in alignment of the respective fluid conduits meeting in a device such as a union is to utilize a single adaptor sleeve which is shared by both tubes where the tubes meet at the union. A union can also have no central web, where the drilled-through hole is dimensioned such that a single adaptor sleeve can pass directly through the device. In this embodiment, the sharing of a single adaptor sleeve by two tubes may reduce some of the accumulated alignment error, but it is still subject to error arising from diametral clearance between the outer diameters of the respective fused silica tubes, and the inner diameter of the adaptor sleeve.

More importantly, there is now no feature of the union which dictates the insertion distance for the respective tubes upon assembly, and the junction region is not accessible to view. Attainment of a liquid-tight seal requires that the junction between the respective fused silica tube ends lies in a region of the adaptor sleeve between the zones of compression produced by the respective ferrules. Accomplishing this on small parts without the assistance of additional fixturing is difficult. This approach is very susceptible to damaging the relatively fragile fused silica tubing ends because assembly of the union in the field, in the absence of visual cues or dedicated fixturing, typically involves a manual process of feeling for contact between the inserted fused silica tube ends, and then holding that contact while tightening is performed on the compression screws.

Moreover, during the tightening of a conventional compression-type fitting, the action of the compression screw tends to impart both a rotational and an axial motion to the adaptor sleeve as the ferrule and sleeve are deformed. This combination of motions tends to drive the fused silica tube end into grinding contact with the opposing tube end, or with the bottom of the port detail when a shared sleeve is not used. This grinding contact can further aggravate the fracturing of the raw fused silica tube end.

Additionally, a compression fitting with adaptor sleeve and ferrule relies on a friction-type connection to retain the fused silica tubing within the sleeve. With conventional stainless steel tubing, an adequately tightened stainless steel ferrule will create a local deformation in the underlying tube such that the tube will not extract from the ferrule in response to normal chromatographic pressures. When a PEEK or other polymeric adaptor sleeve is compressed onto a fused silica tube, though the ferrule may create a deep deformation in the adaptor sleeve, there is substantially no corresponding deformation created by the adaptor sleeve in the fused silica tubing. Therefore, in the presence of high chromatographic pressure, retention of the fused silica tube within the sleeve relies upon friction between the polymeric sleeve and the polyimide buffer coating of the fused silica, or between the polymeric sleeve and a bare fused silica surface. In either case, a common mode of failure is ejection of the fused silica tube from the compression fitting as liquid pressure is increased.

SUMMARY OF THE INVENTION

The present invention is a fluidic terminal as well as a method for producing such fluidic terminals. According to the invention, a fluid conduit such as a fused silica capillary tube is provided with a dedicated termination which is bonded to the conduit. The bond is obtained by high-temperature processing which achieves liquefaction and reflow of a thermoplastic polymer in the bond region. The thermoplastic polymer is chosen from a class of polymers which demonstrates a high degree of chemical inertness at room temperature, which class includes the polyaryl ether ketones. The polymer is further selected based on its ability to generate a suitable bond with the substrates comprising the terminal and the fluid conduit, that bond being required to withstand the imposed mechanical and hydraulic stresses and to maintain a fluid-tight seal. One such polymer is polyether-ether-ketone (PEEK). The stiffness and strength of PEEK are useful in achieving structures capable of elevated pressure operation. Depending upon the service requirements, alternate chemically inert thermoplastic polymers may be employed. Those polymers include the melt-processable or thermoplastic fluoropolymer materials such as fluorinated ethylene-propylene (FEP), perfluoroalkoxy tetrafluoroethylene (PFA), and ethylene tetrafluoroethylene (ETFE). The class of useful polymers further includes the thermoplastic polyimides, polyphenylenes, and polyolefins. The thermoplastic polymer may be compounded or provided with filler materials such as glass or carbon to modify the mechanical or the thermal properties to suit the application.

The terminal is configured to permit an interface with a corresponding terminal on another fluid conduit, or with an appropriately configured port located on another component of a hydraulic circuit. The terminal is further configured to produce an interface junction which is characterized by cleanly-swept geometry with substantially no dead-volume. The terminal provides mechanical containment for the inserted fluid conduit, imparting additional mechanical robustness to the end of the conduit. The terminal is configured to interact cooperatively with a mating terminal or mating port in order to achieve the alignment specifications necessary for proper junction performance at a capillary separation size scale. The bonded terminal is further configured to provide high resistance to expulsion of the inserted conduit.

Embodiments of the terminal are shown which facilitate the interface of fused silica capillaries to other capillaries, to manifolds, and to existing compression-type ports as may exist on system components such as pumps or sample injectors.

DETAILED DESCRIPTION OF THE INVENTION

For the method of the present invention, the surface area where bonding occurs on each of the components of the terminal must be large enough that the stresses resulting from in-use loads can be accommodated. For example, when bonding a 375 micron outside diameter fused silica capillary into a stainless steel terminal, an insertion length of 0.375" will result in a bond area of approximately 0.017393 square inches at the outside diameter of the capillary. A fluid pressure of 20,000 PSI acting on the exposed cross-section of the capillary of 0.00017119 square inches will produce an expulsion force of 3.42 pounds. If the expulsion force is distributed substantially uniformly over the bond area of 0.017393 square inches, a shear stress of approximately 197 PSI is produced at the capillary bond line.

The bonding material used in the terminal is a thermoplastic polymer selected from the group consisting of the polyaryl ketones, thermoplastic fluoropolymers, polyimides, polyphenylenes, and polyolefins. The polymer may be unfilled, or may be compounded with other materials such as carbon or glass to modify the mechanical or the thermal properties obtained. A preferred material of the class of polyaryl ketones is polyether ether ketone (PEEK). PEEK exhibits a high degree of solvent resistance, mechanical strength and stiffness, and an ability to generate a fluid-tight seal between the terminal and the capillary.

Preferred embodiments of the terminal are designed with containment of the liquefied polymer in mind. Since essentially any components that come into contact with the liquefied polymer at the bonding temperature will remain bonded after cool down, it is preferred that the joint be self-fixturing, that is, the components to be bonded are designed so that the intended component orientation is maintained, and the liquefied polymer is prohibited from escaping the bond area, without the introduction of other containment or orientation surfaces in contact with the polymer. An alternative approach is to provide liquefied polymer containment with a sacrificial surface such as a metal foil, which may either be left in place after cool down, or machined away as necessary.

Appropriately configured components are assembled at room temperature, and any additional support (external fixturing which is out of contact with the polymer) as necessary and commonly known in the art is provided. The parts should be substantially free of surface contamination. It is generally not necessary to etch, prime, or otherwise modify the surfaces to be bonded, but the option of performing surface modification to increase bond surface area, obtain mechanical keying, or to achieve chemical activation of the surfaces is available.

In a preferred embodiment, the polymer is supplied to the bond area as a preform, in a manner analogous to that used in brazing. The polymer preform is inserted into the assembly, and any preloading (if used) is supplied. Preloading can be accomplished by gravity, coil springs, leaf springs, lever arms, or other suitable means. When the polymer rod or tube preforms are long enough that the end in contact with the preload hardware is maintained away from high temperature, there is no concern with the preload hardware becoming bonded to the workpiece.

The heat used to achieve component bonding may be supplied in any appropriate method, depending upon the geometry of the components being bonded, and upon the requirements of any external fixturing. One method for localized heating can be attained by inserting the components into corresponding cavities in a block of aluminum or steel, and heating that block by means of resistive heater cartridges or a heated platen. Alternatively, the components and any necessary fixturing can be heated within an industrial oven. Other options for heating, such as induction heating, ultrasonic heating, or laser-based heating are available and any suitable method may be used.

The components to be bonded are preferably taken up to temperature over a timeframe of several minutes. This relatively slow heating cycle allows for good regulation of temperature as the setpoint is reached, and allows the polymer preform to liquify in a predictable manner to produce a high quality joint, free of entrained air. Substantial temperature overshoot is generally undesirable in this application since the polymer is being taken to a temperature where overshoot could result in thermal breakdown or decomposition of the material. In a preferred embodiment incorporating PEEK as the thermoplastic polymer, the components are typically maintained at a temperature between 385° C. and 420° C. for 1 to 3 minutes, although the invention is not limited to such. This is a temperature range within which the PEEK polymer can achieve proper bonding to the components. In one embodiment, a non-oxidizing atmosphere may be provided around the workpieces during heating.

After the heating cycle is completed, the components and any associated thermal mass are allowed to return to room temperature passively although the cooling may be accelerated by any suitable method that maintains the chemical and structural integrity of the terminal.

Figure 1:
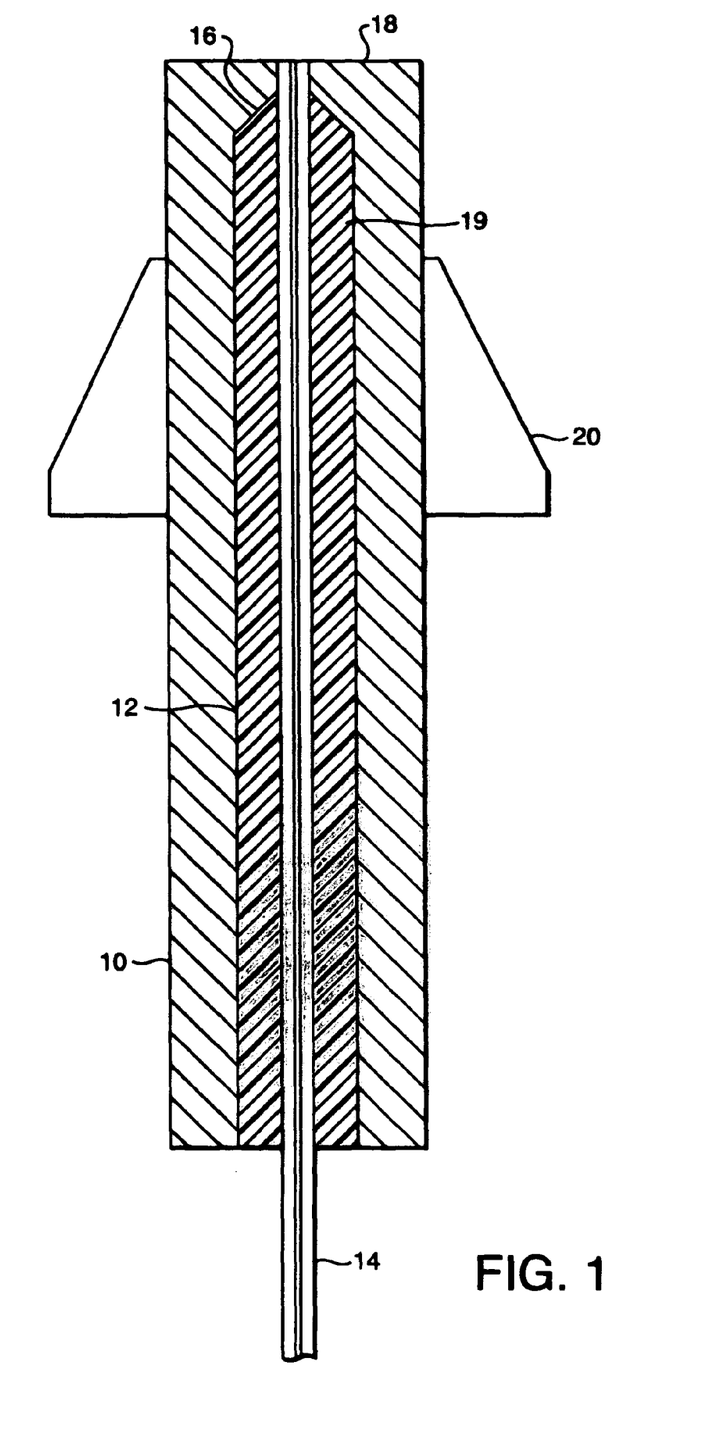
FIG. 1 is a sectional representation of one embodiment of the apparatus of the present invention.

An embodiment of the fluidic terminal disclosed herein is shown in a sectional view in FIG. 1. In a preferred embodiment, the terminal housing 10 is constructed from stainless steel, that material providing a reasonable combination of strength, stiffness, chemical inertness, machineablity, and heat stability. The material chosen for the terminal should be resistant to cold flow or creep in the presence of the forces involved in sealing at high pressure. Examples of alternative materials for the terminal include titanium, nickel, and certain ceramics.

The housing 10 may be generated from centerless ground stock, in which case the diametral dimension and the cylindricity may be held to extremely tight tolerances. The geometry of the housing 10 is adapted to interface with an existing conical compression-type port detail or conical sealing interface on a system component such as a pump or sample injector. The proximal end face 18 may be ground and optionally lapped or polished to produce the desired right-circular cylindrical shape and surface finish.

The housing has an axial bore 12 which allows a conduit, preferably a fused silica tube, 14 to pass through. In a preferred embodiment, the bore is graduated at its proximal portion 16. Alternatively, the bore 12 may be generated with two different diameters, with a smaller diameter at the proximal portion. In both embodiments, the larger of the diameters penetrates through the majority of the terminal housing, but does not carry through the proximal face 18. The proximal face 18 is breached by the fused silica tube 14. The lumen of the tube 14 is typically open at both ends. The fused silica tube 14 may have a polymide coating.

Due to the graduation of the axial bore 12 in the proximal portion 16, the housing 10 converges to a substantially line-to-line fit between itself and the tube 14 at or near the proximal face 18 and the proximal tube opening. The close tolerance employed in this region is used to establish the concentricity between the tube 14 and the outer diameter of the housing 10. The substantially line-to-line fit between the housing 10 and the tube 14 is also used to retain the molten polymer during reflow processing. This aspect yields a preferred self-fixturing embodiment.

For interfacing with existing high-pressure ports utilizing compression-type fittings, the terminal may be used in conjunction with a stainless steel ferrule 20 and compression screw (not shown) as are known in the art.

Prior to heat cycling, polymer volume 19 is substantially filled with the thermoplastic in the form of a hollow cylindrical preform interposed between axial bore 12 and fused silica tube 14. The thermoplastic may be introduced to the bore cavity by any suitable means. Preforms can take any variety of shapes including ribbons, films, sleeves, rings or powders.

One method of this invention provides for heating the terminal to melt the thermoplastic contained within the bore and surrounding the tube. When the thermoplastic and associated terminal components have achieved the necessary bonding temperature, and are subsequently cooled, the tube and terminal are bonded to each other.

Figure 2:
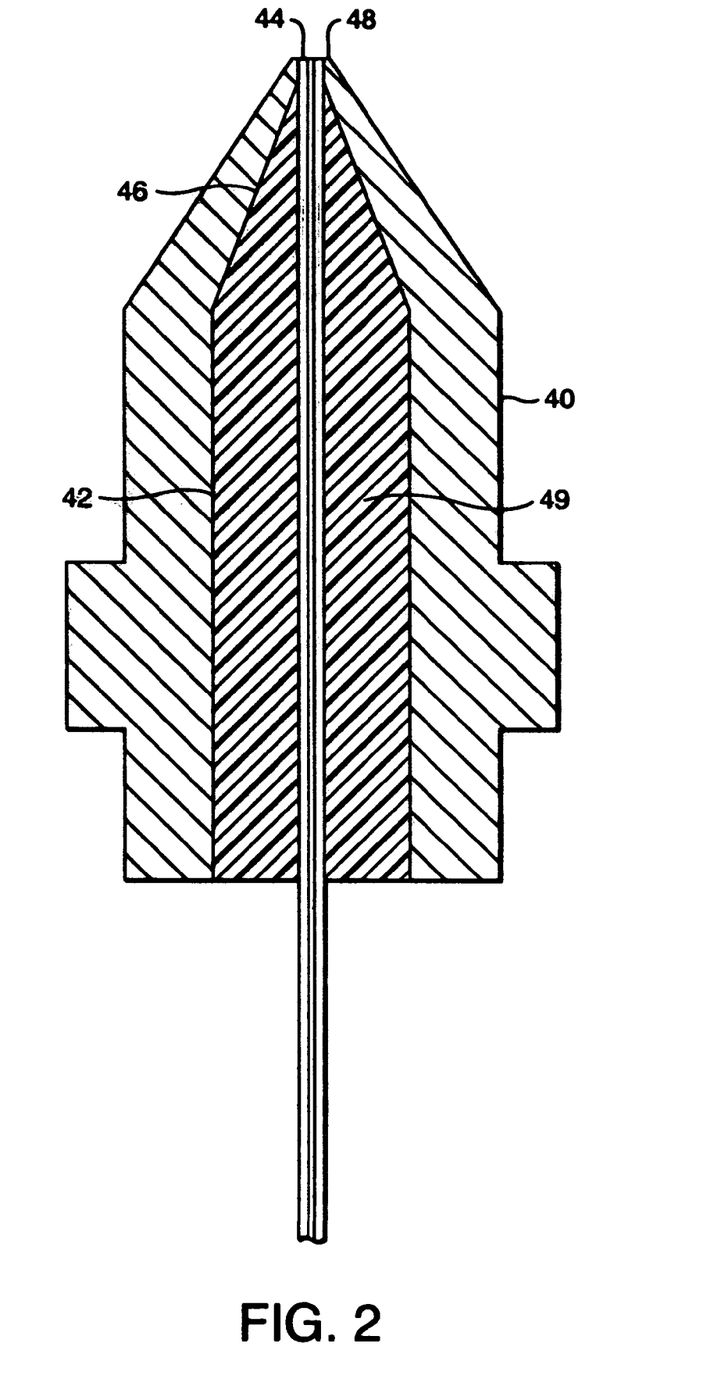
FIG. 2 is a sectional representation of a second embodiment of the apparatus of the present invention.

FIG. 2 depicts an embodiment where the geometry of the terminal housing 40 is adapted to provide a conical sealing interface immediately adjacent to proximal face 48, in contrast to the ferrule-based seal depicted in FIG. 1. Terminal housing 40 has an axial bore 42 that allows the conduit 44, preferably a fused silica tube, to pass through. In a preferred embodiment, the axial bore is graduated at its proximal portion 46. The proximal face 48 of terminal housing 40 is breached by the fused silica tube 44 at its proximal opening. The lumen of the tube 44 is typically but not necessarily open at both ends.

Due to the graduation of the axial bore in the proximal portion 46, the housing 40 converges to a substantially line-to-line fit between itself and the tube 44. The close tolerance employed in this region is used to establish the concentricity between tube 44 and the outer diameter of the proximal face 48. The substantially line-to-line fit between terminal housing 40 and tube 44 is also used to retain the molten polymer during reflow processing. This aspect again yields a preferred self-fixturing embodiment. Prior to heat cycling, polymer volume 49 is substantially filled with the thermoplastic in the form of a hollow cylindrical preform interposed between axial bore 42 and fused silica tube 44, although any other method may be used. When the thermoplastic and associated terminal components have achieved the necessary bonding temperature, and are subsequently cooled, the tube and terminal are bonded to each other.

Figure 3:
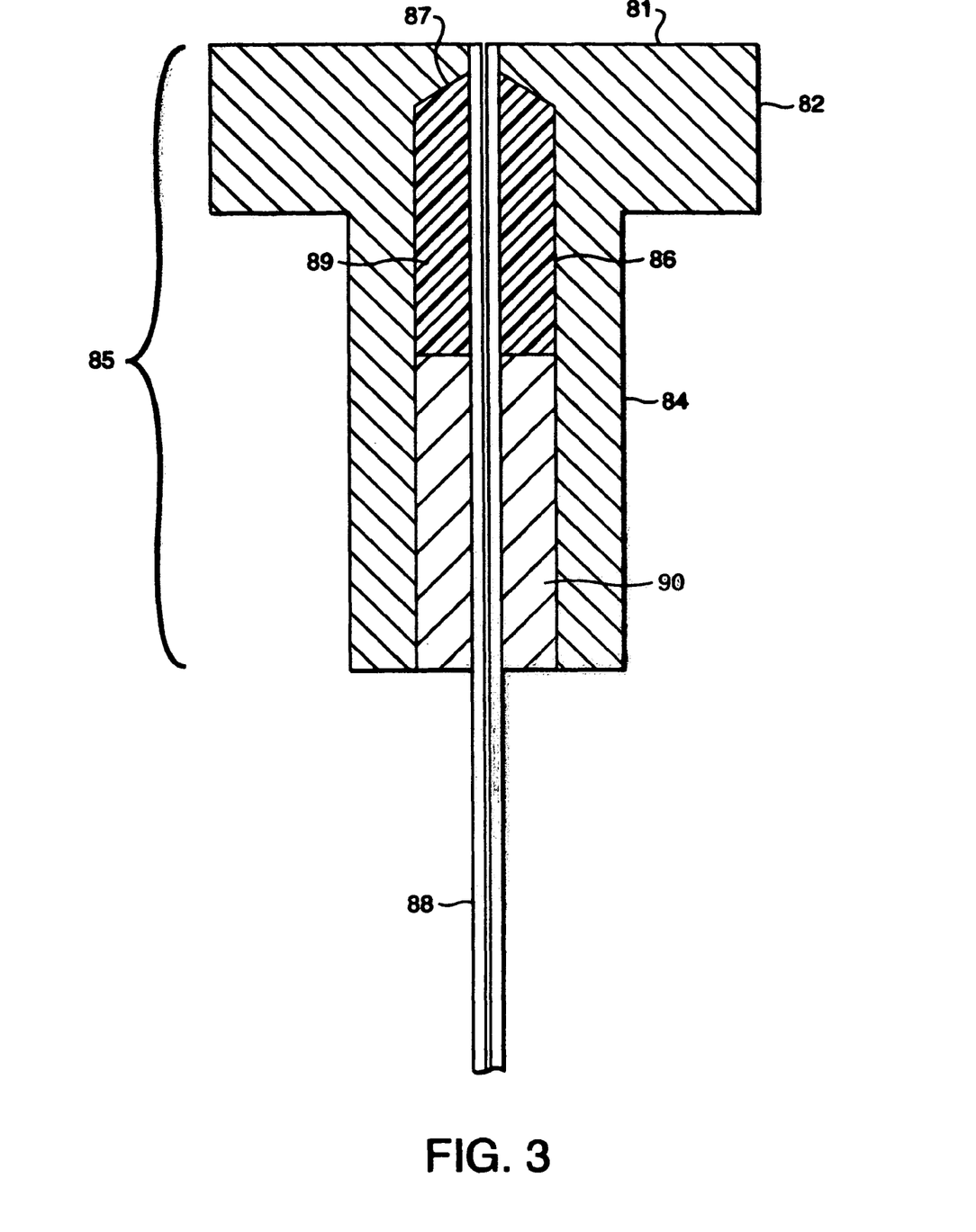
FIG. 3 is a sectional representation of a third embodiment of the apparatus of the present invention.

FIG. 3 depicts an alternate embodiment of a terminal of the present invention. This embodiment provides a substantially planar proximal face 81 adapted to seal to a planar port or planar sealing interface such as a manifold, or to provide a substantially zero-volume interface or union between two or more tubes.

The terminal of FIG. 3 has a cylindrical flange portion 82 at its proximal end and a cylindrical body portion 84 at its distal end. The body portion 84 is of smaller diameter than the flange portion 82. The body 84 and flange 82 make up a unitary terminal housing 85.

An axial bore 86 passes through the housing 85. In a preferred embodiment, the bore is graduated at its proximal portion 87. Alternatively to all of the shown embodiments, the bore may be generated with two different diameters, with a smaller diameter at the proximal portion. In either case, the larger of the diameters penetrates through the majority of the terminal housing 85, but does not carry through the proximal face 81. The proximal face 81 is breached by the fused silica tube 88 at its proximal opening. The lumen of the tube 88 is typically but not necessarily open at both ends.

Due to the graduation of the axial bore 86 in the proximal portion 87, the housing 85 converges to a substantially line-to-line fit between itself and the tube 88. The close tolerance employed in this region is used to establish the concentricity between tube 88 and the outer diameter of the cylindrical flange 82. The substantially line-to-line fit between terminal housing 85 and tube 88 is also used to retain the molten polymer during reflow processing. This aspect again yields a preferred self-fixturing embodiment. Prior to heat cycling, polymer volume 89 is substantially filled with the thermoplastic in the form of a hollow cylindrical preform interposed between axial bore 86 and fused silica tube 88, although any other method may be used. Polymer volume 89 is further bounded by backing sleeve 90. Backing sleeve 90 has a hollow cylindrical form and is preferably constructed from the same material as the terminal housing. Prior to heating, a radial clearance dimension of typically 0.001" to 0.003" exists between the outer diameter of backing sleeve 90 and axial bore 86. Also prior to heating, a radial clearance dimension of typically 0.001" to 0.003" exists between the inner diameter of backing sleeve 90 and the outer diameter of fused silica tube 88. During the heating cycle, backing sleeve 90 is advanced into the molten polymer, by application of a force typically supplied by spring-loaded fixturing. The advance of backing sleeve 90 into the molten polymer is useful in achieving polymer contact and wetting of all surfaces to be bonded. Backing sleeve 90 becomes bonded into terminal housing 85 as molten polymer flows and fills the radial clearances at the outer and inner diameters of the sleeve, and is subsequently cooled. The existence of a rigid backing sleeve bonded within axial bore 86 can contribute significantly to the high-pressure capability of the fluidic terminal, by augmenting the resistance to expulsion of the bonded components. A backing sleeve may be used with any of the fluidic terminals described herein.

Figure 4A:
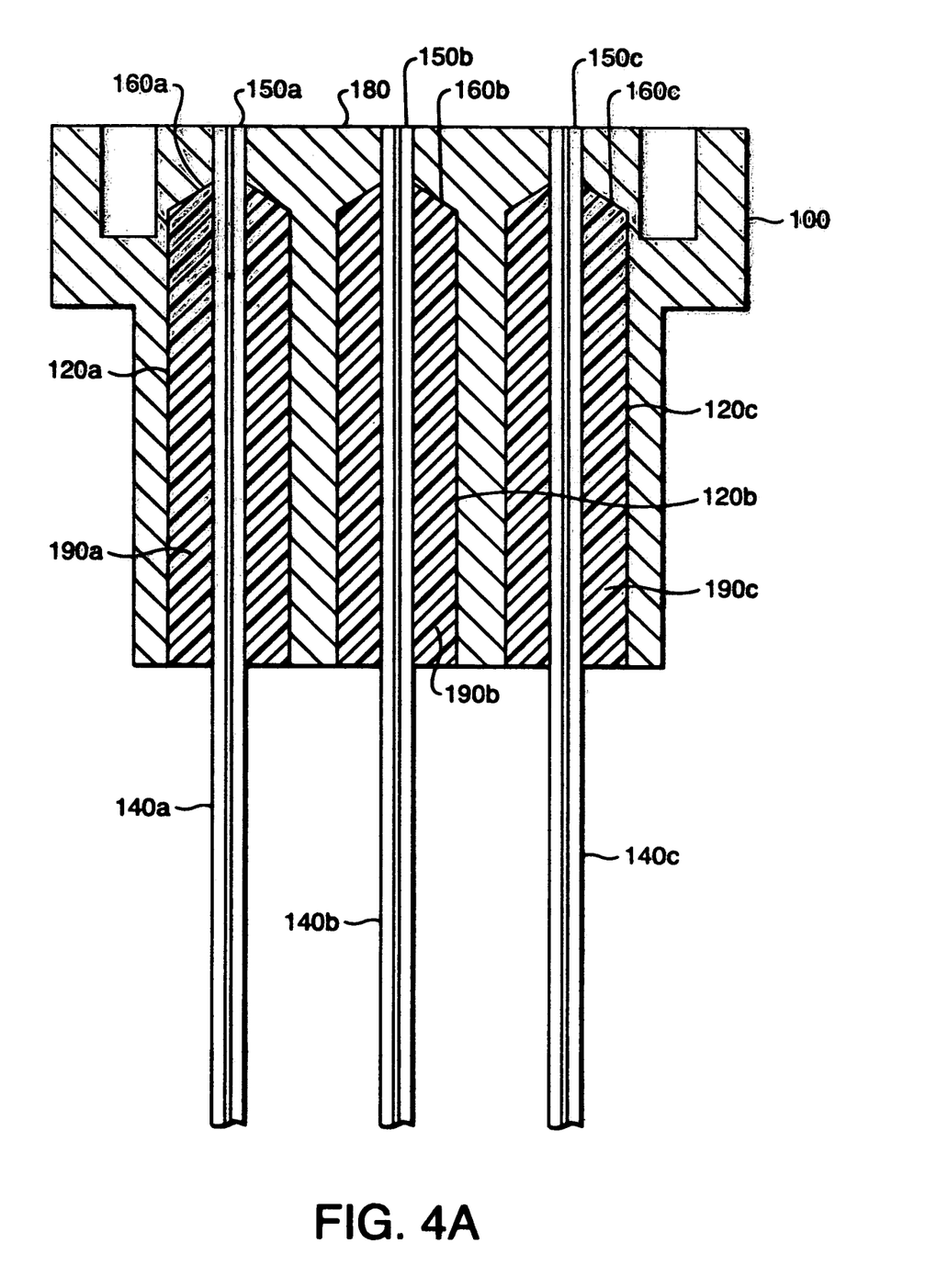
FIG. 4A is a sectional representation of a fourth embodiment of the apparatus of the present invention.

FIG. 4A shows a terminal housing 100 wherein the proximal face 180 is a planar surface housing the proximal ends of three conduits 140a, 140b, 140c. Each of the conduits 140a, 140b, and 140c has at least one proximal end 150a, 150b and 150c defining a proximal opening in the conduit or the conduit lumen. Each of the conduits 140a, 140b, and 140c has an axis running parallel to the flow of fluid through the conduit.

Terminal housing 100 has bores 120a, 120b, and 120c that allow the conduits 140a, 140b, and 140c, which are preferably fused silica tubes, to pass through. In a preferred embodiment, the bores are graduated at their proximal portions 160a, 160b, and 160c. The proximal face 180 of terminal housing 100 is breached by the fused silica tube conduits 140a, 140b, and 140c.

Due to the graduation of the bores in the proximal portions 160a, 160b, and 160c, terminal housing 100 converges to a substantially line-to-line fit between itself and the conduits 140a, 140b, and 140c. The close tolerance employed in this region is used to establish a defined orientation between the lumens of the fluid conduits. Preferably, the housing holds conduits 140a, 140b, and 140c in alignment wherein the axis of each conduit is substantially parallel to each other, and at least one proximal end of each conduit 150a, 150b, and 150c is aligned about the planar proximal face 180.

The substantially line-to-line fit between terminal housing 100 and conduits 140a, 140b, and 140c is also used to retain the molten polymer during reflow processing. This aspect again yields a preferred self-fixturing embodiment. Prior to heat cycling, the bores 120a, 120b, and 120c are provided with hollow cylindrical thermoplastic preforms which substantially fill respective polymer volumes 190a, 190b, and 190c, although any other method may be used. The preforms are reflowed by heating to obtain a fluid-tight seal between terminal housing 100 and conduits 140a, 140b, and 140c, in accordance with the invention.

Figure 4B:
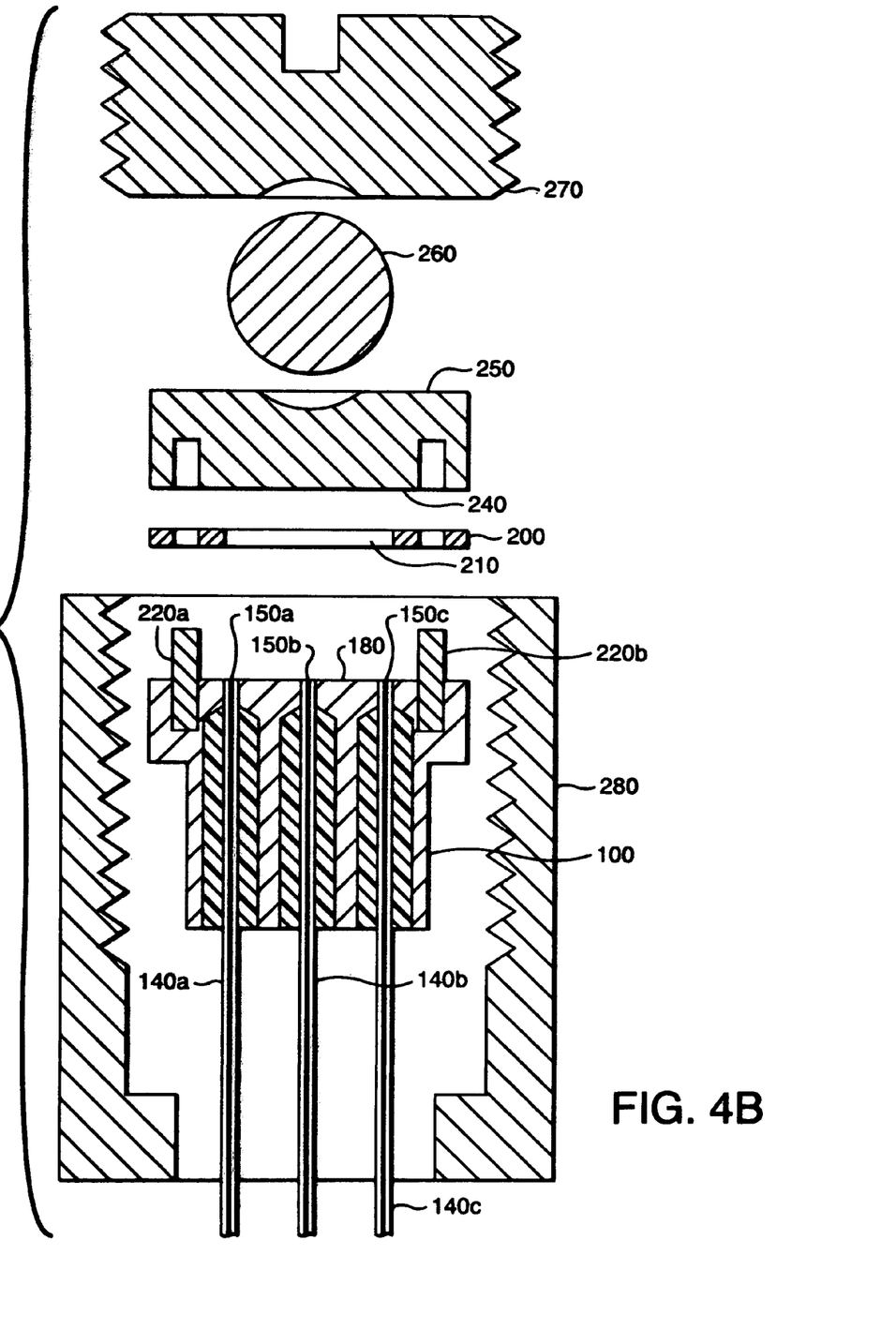
FIG. 4B is an exploded sectional representation of an assembly incorporating the terminal embodiment of FIG. 4A.

FIG. 4B shows the fluidic terminal of FIG. 4A used in conjunction with a gasket element and a cap element to implement a low band-broadening tee. The gasket 200 has a channel 210 in fluid communication with the proximal openings 150a, 150b, 150c of conduits 140a, 140b, and 140c. Gasket 200 is maintained in position with respect to proximal openings 150a, 150b, and 150c by its engagement with alignment pins 220a and 220b mounted in terminal housing 100. In a preferred embodiment, gasket 200 is generated by the mask-controlled photochemical etching of stainless steel sheet. The stainless steel gasket may optionally have a relatively softer surface layer such as deposited gold or fluoropolymer on one or more surfaces.

The planar fluid path defined by channel 210 in gasket 200 is sealed on one surface by proximal face 180 of terminal housing 100, and is sealed on the opposing surface by cap planar surface 240 of cap element 250. Cap element 250 shares alignment pins 220a, 220b with gasket 200, although its planar surface 240 does not require exact registration with either gasket 200 or terminal housing 100. Ball element 260 is used to achieve angular decoupling of cap element 250 from the mechanism which applies the sealing force to the assembly, thereby producing a more uniform loading of the sealing plane. In the embodiment of FIG. 4B, the sealing stress is supplied by screw 270 which engages internally-threaded housing 280, and maintains the captured tee components in compression.

Accordingly, it should be readily appreciated that the device and method of the present invention has many practical applications. Additionally, although the preferred embodiments have been illustrated and described, it will be obvious to those skilled in the art, that various modifications can be made without departing from the spirit and scope of this invention. Such modifications are to be considered as included in the following claims.

What is claimed:

1. A fluidic terminal comprising:
two or more conduits for transporting fluid, each of the two or more conduits having a proximal end, a proximal opening and a distal end;
a substantially cylindrical housing having two or more axial bores and a proximal face, each of the two or more axial bores having a cylindrical portion and a proximal portion, the proximal end of each conduit positioned in an axial bore of the two or more axial bores, the axial bores and the conduits extending along a common axis, a volume of the cylindrical and proximal portions of the axial bores not occupied by the conduits being backfilled with a thermoplastic polymer, the proximal ends of the conduits extending through the axial bores to the proximal face of the substantially cylindrical housing, and the thermoplastic polymer bonded to the conduits and the substantially cylindrical housing to provide a fluid-tight seal between the conduits and the substantially cylindrical housing, wherein the proximal face is a planar surface housing the proximal ends of the two or more conduits, wherein the planar surface of the proximal face is in sealed engagement with a planar surface of a cap element, and wherein a gasket is set between the cap element and the planar proximal face providing a fluidic seal.

2. A fluidic terminal as in claim 1 wherein:
the gasket has a channel in fluid communication with the proximal openings in the conduits.

3. A fluidic terminal comprising:
two or more conduits for transporting fluid, each of the two or more conduits having a proximal end, a proximal opening and a distal end;
a substantially cylindrical housing having two or more axial bores and a proximal face, each of the two or more axial bores having a cylindrical portion and a proximal portion, the proximal end of each conduit positioned in an axial bore of the two or more axial bores, the axial bores and the conduits extending along a common axis, a volume of the cylindrical and proximal portions of the axial bores not occupied by the conduits being backfilled with a thermoplastic polymer, the proximal ends of the conduits extending through the axial bores to the at least proximal face of the substantially cylindrical housing, and the thermoplastic polymer bonded to the conduits and the substantially cylindrical housing to provide a fluid-tight seal between the conduits and the substantially cylindrical housing, wherein the proximal face is a planar surface housing the proximal ends of the two or more conduits, wherein the planar surface of the proximal face is in sealed engagement with a planar surface of a cap element, wherein at least one of the planar proximal face and the cap element planar surface has a channel in fluid communication with the proximal openings of the conduits, the channel including two or more fluid paths, each fluid path defined by at least one of the conduits, and wherein a gasket is set between the cap element and the planar proximal face providing a fluidic seal.

4. A fluidic terminal as in claim 3 wherein:
at least one of the two or more conduits is a fused silica tube.

5. A fluidic terminal as in claim 4 wherein:
the fused silica tube has a polyimide coating.

6. A fluidic terminal as in claim 3 wherein:
the housing is stainless steel.

7. A fluidic terminal as in claim 3 wherein:
the housing is generated from centerless ground stock.

8. A fluidic terminal as in claim 3 wherein:
the diameter of each axial bore at a proximal end narrows to substantially meet the outer diameter of a corresponding conduit of the two or more conduits at the proximal face.

9. A fluidic terminal as in claim 3 wherein:
the proximal ends of the conduits extend beyond the proximal face of the housing.

10. A fluidic terminal as in claim 3 wherein:
the housing and proximal face provide a fluidically sealable interface with a port.

11. A fluidic terminal as in claim 10 wherein:
the housing provides a substantially planar sealing interface to complement the port.

12. A fluidic terminal as in claim 10 wherein:
the housing provides a substantially conical sealing interface to complement the port.

13. A fluidic terminal as in claim 3 wherein:
the polymer is selected from the group consisting of poly aryl ketones, fluoropolymer ketones and polyolefins.

14. A fluidic terminal as in claim 13 wherein:
the poly aryl ketones include a poly aryl ether ketone.

15. A fluidic terminal as in claim 14 wherein:
the poly aryl ether ketone is a poly ether ether ketone.

16. A fluidic terminal as in claim 3 further comprising:
a substantially cylindrical flange positioned at a proximal end of the housing.

17. A fluidic terminal as in claim 3 wherein:
the planar proximal face has a channel traversing the proximal openings of the conduits.

18. A fluidic terminal as in claim 3 wherein:
the gasket has a channel in fluid communication with the proximal openings in the conduits.

* * * * *